(12) United States Patent
Janna et al.

(10) Patent No.: US 9,539,037 B2
(45) Date of Patent: Jan. 10, 2017

(54) ORTHOPAEDIC IMPLANTS

(75) Inventors: Sied W. Janna, Memphis, TN (US);
Nicholas S. Ritchey, Collierville, TN (US); Graham Ralph Keltner, Hernando, MS (US); Henry B. Faber, Memphis, TN (US); Kohsuke Watanabe, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 194 days.

(21) Appl. No.: 13/701,548

(22) PCT Filed: Jun. 3, 2011

(86) PCT No.: PCT/US2011/039121
§ 371 (c)(1),
(2), (4) Date: Feb. 7, 2013

(87) PCT Pub. No.: WO2011/153468
PCT Pub. Date: Dec. 8, 2011

(65) Prior Publication Data
US 2013/0131679 A1     May 23, 2013

Related U.S. Application Data

(60) Provisional application No. 61/351,142, filed on Jun. 3, 2010.

(51) Int. Cl.
*A61B 17/72* (2006.01)
*A61B 17/17* (2006.01)

(52) U.S. Cl.
CPC ........... *A61B 17/72* (2013.01); *A61B 17/1707* (2013.01); *A61B 17/1725* (2013.01)

(58) Field of Classification Search
CPC ........................................ A61B 17/72–17/7291
USPC ....................................................... 606/62–68
See application file for complete search history.

(56) References Cited

U.S. PATENT DOCUMENTS

| | | | |
|---|---|---|---|
| 3,219,969 | A | 11/1965 | Snavely |
| 4,353,110 | A | 10/1982 | Ellis |
| 4,532,599 | A | 7/1985 | Smith |
| 4,621,628 | A | 11/1986 | Brudermann |
| D297,047 | S | 8/1988 | Hon |
| 4,794,930 | A | 1/1989 | Machida et al. |
| 4,803,976 | A | 2/1989 | Frigg et al. |

(Continued)

FOREIGN PATENT DOCUMENTS

| | | |
|---|---|---|
| CA | 2571508 C | 3/2012 |
| CN | 1512857 A | 7/2004 |

(Continued)

OTHER PUBLICATIONS

Authorized officer Kim, Myeong Hee, International Search Report in PCT/US2011/039121, mailed Feb. 17, 2012, 9 pages.

(Continued)

*Primary Examiner* — Eduardo C Robert
*Assistant Examiner* — Steven Cotroneo
(74) *Attorney, Agent, or Firm* — Fish & Richardson P.C.

(57) ABSTRACT

An orthopedic implant including a body defining at least one landmark and a probe comprising a sensor spaced apart from the at least one landmark a set distance. The probe and sensor being releasably fixed to the body of the implant to limit movement of the sensor relative to the at least one landmark.

34 Claims, 8 Drawing Sheets

(56) References Cited

U.S. PATENT DOCUMENTS

| | | |
|---|---|---|
| 5,049,151 A | 9/1991 | Durham et al. |
| 5,127,913 A | 7/1992 | Thomas |
| 5,217,009 A | 6/1993 | Kronberg |
| 5,251,127 A | 10/1993 | Raab |
| 5,281,224 A | 1/1994 | Faccioli et al. |
| 5,320,625 A | 6/1994 | Bertin |
| 5,361,766 A | 11/1994 | Nichols et al. |
| 5,383,917 A | 1/1995 | Desai et al. |
| 5,411,503 A | 5/1995 | Hollstien et al. |
| 5,412,185 A | 5/1995 | Sturman, Jr. et al. |
| 5,417,688 A | 5/1995 | Elstrom et al. |
| 5,433,720 A | 7/1995 | Faccioli et al. |
| 5,514,145 A | 5/1996 | Durham et al. |
| 5,580,156 A | 12/1996 | Suzuki et al. |
| 5,584,838 A | 12/1996 | Rona et al. |
| 5,585,783 A | 12/1996 | Hall |
| 5,957,836 A | 9/1999 | Johnson |
| 5,957,934 A | 9/1999 | Rapoport |
| 6,009,878 A | 1/2000 | Weijand et al. |
| 6,036,696 A | 3/2000 | Lambrecht et al. |
| 6,039,742 A | 3/2000 | Krettek et al. |
| 6,074,394 A | 6/2000 | Krause |
| 6,081,741 A | 6/2000 | Hollis |
| 6,106,528 A | 8/2000 | Durham et al. |
| 6,157,853 A | 12/2000 | Blume et al. |
| 6,162,228 A | 12/2000 | Durham |
| 6,174,335 B1 | 1/2001 | Varieur et al. |
| 6,212,419 B1 | 4/2001 | Blume et al. |
| 6,233,490 B1 | 5/2001 | Kasevich |
| 6,267,770 B1 | 7/2001 | Truwit |
| 6,304,091 B1 | 10/2001 | Shahoian et al. |
| 6,311,082 B1 | 10/2001 | Creighton, IV et al. |
| 6,474,341 B1 | 11/2002 | Hunter et al. |
| 6,503,249 B1 | 1/2003 | Krause |
| 6,575,973 B1 | 6/2003 | Shekalim |
| 6,636,757 B1 | 10/2003 | Jascob et al. |
| 6,675,491 B2 | 1/2004 | Sasaki et al. |
| 6,694,168 B2 | 2/2004 | Traxel et al. |
| 6,718,194 B2 | 4/2004 | Kienzle, III |
| 6,747,253 B1 | 6/2004 | Firth et al. |
| 6,807,446 B2 | 10/2004 | Fenn et al. |
| 6,890,332 B2 | 5/2005 | Truckai et al. |
| 6,991,655 B2 | 1/2006 | Iversen |
| 7,001,346 B2 | 2/2006 | White |
| 7,029,478 B2 | 4/2006 | Hollstien et al. |
| 7,060,075 B2 | 6/2006 | Govari et al. |
| D528,211 S | 9/2006 | Solar |
| 7,130,676 B2 | 10/2006 | Barrick |
| 7,152,608 B2 | 12/2006 | Hunter et al. |
| 7,217,276 B2 | 5/2007 | Henderson et al. |
| 7,253,611 B2 | 8/2007 | Ma et al. |
| 7,294,133 B2 | 11/2007 | Zink et al. |
| 7,295,184 B2 | 11/2007 | Suprun et al. |
| 7,358,481 B2 | 4/2008 | Yeoh et al. |
| 7,477,926 B2 | 1/2009 | McCombs |
| 7,532,997 B2 | 5/2009 | Li et al. |
| 7,542,791 B2 | 6/2009 | Mire et al. |
| 7,549,960 B2 | 6/2009 | Govari |
| 7,559,931 B2 | 7/2009 | Stone |
| 7,575,550 B1 | 8/2009 | Govari |
| 7,634,306 B2 | 12/2009 | Sarin et al. |
| 7,686,818 B2 * | 3/2010 | Simon et al. .................. 606/130 |
| 7,702,379 B2 | 4/2010 | Avinash et al. |
| 7,727,240 B1 | 6/2010 | Benton |
| 7,729,742 B2 | 6/2010 | Govari |
| 7,780,681 B2 | 8/2010 | Sarin et al. |
| 7,785,330 B2 * | 8/2010 | Sherman et al. ............... 606/96 |
| 7,835,785 B2 | 11/2010 | Scully et al. |
| 7,840,254 B2 | 11/2010 | Glossop |
| 7,846,162 B2 | 12/2010 | Nelson et al. |
| 7,918,853 B2 | 4/2011 | Watanabe et al. |
| 7,925,068 B2 | 4/2011 | Hoctor et al. |
| 7,927,338 B2 | 4/2011 | Laffargue et al. |
| 7,949,386 B2 | 5/2011 | Buly et al. |
| 7,955,280 B2 | 6/2011 | Radinsky et al. |
| 8,007,448 B2 | 8/2011 | Moctezuma de la Barrera |
| 8,057,479 B2 | 11/2011 | Stone |
| 8,066,706 B2 | 11/2011 | Schlienger et al. |
| 8,083,741 B2 * | 12/2011 | Morgan et al. .................. 606/60 |
| 8,167,823 B2 | 5/2012 | Nycz et al. |
| 8,176,922 B2 | 5/2012 | Sherman et al. |
| 8,197,494 B2 | 6/2012 | Jaggi et al. |
| 8,211,108 B2 | 7/2012 | Matityahu |
| 8,241,296 B2 | 8/2012 | Wasielewski |
| 8,251,994 B2 | 8/2012 | McKenna et al. |
| 8,301,262 B2 | 10/2012 | Mi et al. |
| 8,337,426 B2 | 12/2012 | Nycz |
| 8,400,312 B2 | 3/2013 | Hotokebuchi et al. |
| 8,623,023 B2 | 1/2014 | Ritchey et al. |
| 8,739,801 B2 * | 6/2014 | Rains et al. ................... 128/899 |
| 2002/0032445 A1 | 3/2002 | Fujiwara |
| 2002/0052604 A1 | 5/2002 | Simon et al. |
| 2002/0077540 A1 | 6/2002 | Kienzle et al. |
| 2002/0107445 A1 * | 8/2002 | Govari .......................... 600/437 |
| 2002/0151897 A1 * | 10/2002 | Zirkle, Jr. ...................... 606/62 |
| 2002/0173792 A1 | 11/2002 | Severns et al. |
| 2003/0105470 A1 | 6/2003 | White |
| 2003/0120150 A1 | 6/2003 | Govari |
| 2003/0135211 A1 | 7/2003 | Cho |
| 2003/0153829 A1 | 8/2003 | Sarin et al. |
| 2003/0164172 A1 | 9/2003 | Chumas et al. |
| 2003/0208122 A1 | 11/2003 | Melkent et al. |
| 2004/0011365 A1 | 1/2004 | Govari et al. |
| 2004/0034355 A1 | 2/2004 | Govari et al. |
| 2004/0097952 A1 | 5/2004 | Sarin et al. |
| 2004/0147926 A1 | 7/2004 | Iversen |
| 2004/0230199 A1 | 11/2004 | Jansen et al. |
| 2004/0243148 A1 | 12/2004 | Wasielewski |
| 2004/0254584 A1 | 12/2004 | Sarin et al. |
| 2005/0027301 A1 | 2/2005 | Stihl |
| 2005/0027304 A1 | 2/2005 | Leloup et al. |
| 2005/0035115 A1 | 2/2005 | Anderson et al. |
| 2005/0035116 A1 | 2/2005 | Brown et al. |
| 2005/0043726 A1 | 2/2005 | McHale et al. |
| 2005/0059885 A1 | 3/2005 | Melkent et al. |
| 2005/0070916 A1 | 3/2005 | Hollstien et al. |
| 2005/0075562 A1 | 4/2005 | Szakelyhidi et al. |
| 2005/0075632 A1 | 4/2005 | Russell et al. |
| 2005/0080335 A1 * | 4/2005 | Simon et al. .................. 600/424 |
| 2005/0080427 A1 | 4/2005 | Govari et al. |
| 2005/0085714 A1 | 4/2005 | Foley et al. |
| 2005/0085715 A1 | 4/2005 | Dukesherer et al. |
| 2005/0099290 A1 | 5/2005 | Govari |
| 2005/0124988 A1 | 6/2005 | Terrill-Grisoni et al. |
| 2005/0143726 A1 | 6/2005 | Bortkiewicz |
| 2005/0148855 A1 | 7/2005 | Kienzle et al. |
| 2005/0149050 A1 | 7/2005 | Stifter et al. |
| 2005/0197569 A1 | 9/2005 | McCombs |
| 2005/0228270 A1 | 10/2005 | Lloyd et al. |
| 2005/0242087 A1 | 11/2005 | Anderson et al. |
| 2005/0245821 A1 | 11/2005 | Govari et al. |
| 2005/0261555 A1 | 11/2005 | Guzman |
| 2005/0261700 A1 | 11/2005 | Tuma et al. |
| 2006/0015031 A1 | 1/2006 | Kienzle |
| 2006/0029186 A1 | 2/2006 | De Villiers et al. |
| 2006/0052782 A1 | 3/2006 | Morgan et al. |
| 2006/0074405 A1 | 4/2006 | Malackowski et al. |
| 2006/0084867 A1 | 4/2006 | Tremblay et al. |
| 2006/0095047 A1 | 5/2006 | de la Barrera |
| 2006/0106400 A1 | 5/2006 | Fernandez et al. |
| 2006/0142656 A1 | 6/2006 | Malackowski et al. |
| 2006/0184177 A1 | 8/2006 | Echeverri |
| 2006/0190011 A1 | 8/2006 | Ries |
| 2006/0264731 A1 | 11/2006 | Murphy |
| 2006/0282168 A1 | 12/2006 | Sherman et al. |
| 2006/0287613 A1 | 12/2006 | Amiot et al. |
| 2006/0293593 A1 | 12/2006 | Govari et al. |
| 2006/0293614 A1 | 12/2006 | Radinsky et al. |
| 2007/0093709 A1 | 4/2007 | Abernathie |
| 2007/0129629 A1 | 6/2007 | Beauregard et al. |
| 2007/0162018 A1 | 7/2007 | Jensen et al. |
| 2007/0167744 A1 | 7/2007 | Beauregard et al. |
| 2007/0191827 A1 | 8/2007 | Lischinsky et al. |
| 2007/0208251 A1 | 9/2007 | Anderson et al. |

(56) References Cited

U.S. PATENT DOCUMENTS

| | | |
|---|---|---|
| 2007/0219409 A1 | 9/2007 | Shimizu |
| 2007/0225595 A1 | 9/2007 | Malackowski et al. |
| 2007/0249967 A1 | 10/2007 | Buly et al. |
| 2007/0255132 A1 | 11/2007 | Shalgi et al. |
| 2007/0276370 A1 | 11/2007 | Altarac et al. |
| 2007/0282440 A1 | 12/2007 | Visentin |
| 2008/0015551 A1 | 1/2008 | Feine |
| 2008/0021309 A1 | 1/2008 | Amiot et al. |
| 2008/0039857 A1 | 2/2008 | Giersch et al. |
| 2008/0051910 A1 | 2/2008 | Kammerzell et al. |
| 2008/0071142 A1 | 3/2008 | Gattani et al. |
| 2008/0086145 A1 | 4/2008 | Sherman et al. |
| 2008/0146969 A1 | 6/2008 | Kurtz et al. |
| 2008/0154266 A1 | 6/2008 | Protopsaltis et al. |
| 2008/0221628 A1 | 9/2008 | Milbocker et al. |
| 2008/0228195 A1 | 9/2008 | von Jako et al. |
| 2008/0255560 A1 | 10/2008 | Myers et al. |
| 2008/0255584 A1 | 10/2008 | Beverland et al. |
| 2008/0269596 A1 | 10/2008 | Revie et al. |
| 2008/0281326 A1 | 11/2008 | Watanabe et al. |
| 2008/0281334 A1 | 11/2008 | Zheng et al. |
| 2008/0300597 A1* | 12/2008 | Morgan ............... A61B 5/0031 606/62 |
| 2009/0024023 A1 | 1/2009 | Welches et al. |
| 2009/0054910 A1 | 2/2009 | Zheng et al. |
| 2009/0088756 A1 | 4/2009 | Anderson |
| 2009/0099404 A1 | 4/2009 | Kraus et al. |
| 2009/0099665 A1 | 4/2009 | Taylor et al. |
| 2009/0125117 A1 | 5/2009 | Paradis et al. |
| 2009/0138019 A1 | 5/2009 | Wasielewski |
| 2009/0165573 A1 | 7/2009 | Ledoux et al. |
| 2009/0171370 A1 | 7/2009 | Yoon et al. |
| 2009/0177080 A1 | 7/2009 | Kristan et al. |
| 2009/0222050 A1* | 9/2009 | Wolter et al. .................. 606/286 |
| 2009/0227862 A1 | 9/2009 | Smith et al. |
| 2009/0306665 A1 | 12/2009 | Lerner et al. |
| 2009/0306666 A1 | 12/2009 | Czartoski et al. |
| 2009/0326537 A1 | 12/2009 | Anderson et al. |
| 2010/0041985 A1 | 2/2010 | Simon et al. |
| 2010/0063508 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0100011 A1 | 4/2010 | Roche |
| 2010/0137869 A1 | 6/2010 | Borja et al. |
| 2010/0137871 A1 | 6/2010 | Borja |
| 2010/0145337 A1 | 6/2010 | Janna et al. |
| 2010/0152566 A1 | 6/2010 | Rains et al. |
| 2010/0152573 A1 | 6/2010 | Ritchey et al. |
| 2010/0211177 A1 | 8/2010 | Abdou |
| 2010/0249657 A1 | 9/2010 | Nycz et al. |
| 2010/0249796 A1 | 9/2010 | Nycz |
| 2010/0261998 A1 | 10/2010 | Stiehl |
| 2010/0274121 A1 | 10/2010 | Ritchey et al. |
| 2010/0274253 A1 | 10/2010 | Ure |
| 2010/0274256 A1 | 10/2010 | Ritchey et al. |
| 2010/0274306 A1 | 10/2010 | Pastore et al. |
| 2010/0289491 A1 | 11/2010 | Budker et al. |
| 2010/0312245 A1 | 12/2010 | Tipirneni et al. |
| 2011/0060339 A1 | 3/2011 | de Wekker |
| 2011/0082366 A1 | 4/2011 | Scully et al. |
| 2011/0109311 A1 | 5/2011 | Walsh |
| 2011/0130765 A1 | 6/2011 | Fernandez et al. |
| 2011/0208037 A1 | 8/2011 | Rains et al. |
| 2011/0230886 A1 | 9/2011 | Gustilo et al. |
| 2011/0257518 A1 | 10/2011 | Buly et al. |
| 2011/0270080 A1 | 11/2011 | Crane |
| 2011/0276053 A1 | 11/2011 | Birkbeck et al. |
| 2011/0288600 A1 | 11/2011 | Ritchey et al. |
| 2011/0295108 A1 | 12/2011 | Cox et al. |
| 2011/0295253 A1 | 12/2011 | Bonutti et al. |
| 2012/0010500 A1 | 1/2012 | Couture et al. |
| 2012/0022406 A1 | 1/2012 | Hladio et al. |
| 2012/0035468 A1 | 2/2012 | Ritchey et al. |
| 2012/0059376 A1* | 3/2012 | Rains et al. .................... 606/62 |
| 2012/0091122 A1 | 4/2012 | Ahmad et al. |
| 2012/0101361 A1 | 4/2012 | Rains et al. |
| 2012/0130279 A1 | 5/2012 | Stone |
| 2012/0136402 A1 | 5/2012 | Burroughs |
| 2012/0143047 A1 | 6/2012 | Kimura et al. |
| 2012/0157887 A1 | 6/2012 | Fanson et al. |
| 2012/0184844 A1 | 7/2012 | Gielen et al. |
| 2012/0209117 A1 | 8/2012 | Mozes et al. |
| 2012/0220107 A1 | 8/2012 | Fukuda et al. |
| 2012/0226094 A1 | 9/2012 | Ritchey et al. |
| 2012/0227542 A1 | 9/2012 | Koch |
| 2012/0232561 A1 | 9/2012 | Fernandez |
| 2012/0245647 A1 | 9/2012 | Kunz et al. |
| 2012/0253354 A1 | 10/2012 | Arlettaz et al. |
| 2012/0277752 A1 | 11/2012 | Wasielewski |
| 2012/0283599 A1 | 11/2012 | Borja |
| 2012/0323247 A1 | 12/2012 | Bettenga |
| 2012/0330191 A1* | 12/2012 | Hulliger et al. ............... 600/587 |
| 2012/0330319 A1 | 12/2012 | Birkbeck et al. |
| 2013/0046310 A1 | 2/2013 | Ranawat et al. |
| 2013/0053856 A1 | 2/2013 | Penenberg |
| 2013/0053858 A1 | 2/2013 | Penenberg |
| 2013/0053904 A1 | 2/2013 | Penenberg |
| 2013/0066323 A1 | 3/2013 | Nycz et al. |
| 2013/0131679 A1 | 5/2013 | Janna et al. |
| 2013/0218007 A1 | 8/2013 | Petteys et al. |
| 2013/0289573 A1 | 10/2013 | Heilala et al. |

FOREIGN PATENT DOCUMENTS

| | | |
|---|---|---|
| CN | 269823 Y | 5/2005 |
| CN | 201029876 Y | 3/2008 |
| DE | 102008023760 A1 | 12/2009 |
| EP | 628287 A3 | 4/1995 |
| EP | 523905 B1 | 10/1996 |
| EP | 1391181 A1 | 2/2004 |
| EP | 1570782 A3 | 11/2005 |
| EP | 1382308 B1 | 12/2007 |
| EP | 1570781 B1 | 9/2009 |
| EP | 2130511 A1 | 12/2009 |
| EP | 1563810 B1 | 3/2010 |
| EP | 1743590 B1 | 10/2010 |
| EP | 1803394 B1 | 1/2012 |
| EP | 2294980 | 2/2012 |
| GR | 1005791 B | 1/2008 |
| WO | WO9421209 A1 | 9/1994 |
| WO | WO9500085 A1 | 1/1995 |
| WO | WO9713467 A1 | 4/1997 |
| WO | WO9832387 A1 | 7/1998 |
| WO | WO9947052 A1 | 9/1999 |
| WO | WO0134016 A3 | 10/2001 |
| WO | WO02062250 A1 | 8/2002 |
| WO | WO03073951 A1 | 9/2003 |
| WO | WO03044556 A3 | 11/2003 |
| WO | WO03041611 A3 | 12/2003 |
| WO | WO2004030556 A2 | 4/2004 |
| WO | WO2004001569 B1 | 7/2004 |
| WO | WO2004069063 A1 | 8/2004 |
| WO | WO2004091419 A9 | 12/2004 |
| WO | WO2005000140 A2 | 1/2005 |
| WO | WO2005009303 A1 | 2/2005 |
| WO | WO2003105659 A3 | 3/2005 |
| WO | WO2005023110 A1 | 3/2005 |
| WO | WO2004112610 A3 | 5/2005 |
| WO | WO2005051241 A1 | 6/2005 |
| WO | WO2005087125 A3 | 3/2006 |
| WO | WO2006060632 A1 | 6/2006 |
| WO | WO2006067634 A1 | 6/2006 |
| WO | WO2006109983 A1 | 10/2006 |
| WO | WO2005084572 A3 | 11/2006 |
| WO | WO2006128301 A1 | 12/2006 |
| WO | WO2005120203 A3 | 2/2007 |
| WO | WO2007025191 A1 | 3/2007 |
| WO | WO2007009088 A3 | 5/2007 |
| WO | WO2006094119 A3 | 11/2007 |
| WO | Wo2007133168 A2 | 11/2007 |
| WO | WO2008014618 A1 | 2/2008 |
| WO | WO2008105874 A1 | 9/2008 |
| WO | WO2008106593 A2 | 9/2008 |

(56) References Cited

FOREIGN PATENT DOCUMENTS

| | | |
|---|---|---|
| WO | WO2008106593 A3 | 11/2008 |
| WO | WO2009046547 A1 | 4/2009 |
| WO | WO2007061890 A3 | 5/2009 |
| WO | WO2009062314 A1 | 5/2009 |
| WO | WO2009108214 A1 | 9/2009 |
| WO | WO2009131999 A3 | 1/2010 |
| WO | WO2010011978 A1 | 1/2010 |
| WO | WO2010028046 A1 | 3/2010 |
| WO | WO2010030809 A1 | 3/2010 |
| WO | WO2010063117 A1 | 6/2010 |
| WO | WO2010111272 A1 | 9/2010 |
| WO | WO2010052500 A3 | 10/2010 |
| WO | WO2010129141 A3 | 1/2011 |
| WO | WO2010099247 A3 | 2/2011 |
| WO | WO2010129308 A3 | 3/2011 |
| WO | WO2011060536 A1 | 5/2011 |
| WO | WO2011124661 A1 | 10/2011 |
| WO | WO2012080840 A1 | 6/2012 |
| WO | WO2012084739 A1 | 6/2012 |
| WO | WO2012100825 A1 | 8/2012 |
| WO | WO2013049534 A1 | 4/2013 |
| WO | WO2013025927 A3 | 5/2013 |

OTHER PUBLICATIONS

Szakelyhidi, David C., Jr.; "Development of a Magnetic Targeting Device Applied to Interlocking of Distal Intramedullary Nail Screw Holes."; Thesis submitted to the Faculty of Virginia Polytechnic Institute and State University, 25 pages. May 2002 Blacksburg, Virginia.

"Innomed Hip Instruments—hohmann retractors," reprinted from http://www.innomed.net/hip_rets_hohmanns.htm on Jan. 6, 2011, 8 pages.

Association of Surgical Technologists, "AST Recommended Standards of Practice for Surgical Drapes," effective Apr. 13, 2008.

Ashar, Tom, "Ultrasound Guidance for Placement of Central Venous Catheters," Israeli Journal of Emergency Medicine, vol. 7, No. 2, Jun. 2007.

Buckner, C., et al., "Real-Time Sonography wth Electromagnetic Tracking Navigation for Biopsy of a Hepatic Neoplasm Seen on on Arterial Phase Computed Tomography," J Ultrasound Med 2011, 30:253-256.

"GE Heathcare: Ultrasound Imaging Accessories, vol. 6," CIVco Medical Solutions, Multi-Modality Imaging, 2011.

"Guiding Star with the LIDIS module," Ekliptik, 2007.

Ekliptik, LIDIS module, brochure, 2010.

Brochure for GE Healthcare Drapes and Sterile Covers, accessed on Jun. 21, 2012, at http://www.gehealthcare.com/usen/xr/surgery/docs/SurgeryDrapes&Film.pdf.

Ekliptik, "User Manual: Guiding Star/LIDIS," Jun. 16, 2010, reprinted from http://www.ekliptik.si/html/downloads/documents/manuals/LIDIS_user_manual.pdf.

Medtronic, "Orthopaedic Navigation Solutions," 2005, reprinted from http://behzadisportsdoc.com/wordpress/wp-content/uploads/2011/05/medtronic_orthonavsolutions.pdf.

GE Healthcare, "Interventional X-ray, OEC C-arm," 2012.

Ekliptik, Guiding Star, Lidis: The Best Solution for Distal Interlocking, 2008, 2 pages.

Ekliptik, "Guiding Star", reprinted from http://ekliptik.si/contentiview/37/42, on Jul. 1, 2010, 2 pages.

"ORIF—Axial compression plating" [online] [Retrieved on Apr. 23, 2012]; Retrieved from the Internet URL: https://www2.aofoundation.org/wps/portal/surgery?showPage=redfix&bone=Tibia&segment=Shaft&classification=42-A3&teatment=&method=ORIF%20-%20Open%20reduction%20internal%20fixation&implantstype=Compression%20plating&approach=&redfix_url=1285239037789&Language=en; 5 pages.

* cited by examiner

ORTHOPAEDIC IMPLANTS

CROSS REFERENCE TO RELATED APPLICATION

This application claims priority to and the full benefit of U.S. Provisional Application Ser. No. 61/351,142, filed Jun. 3, 2010, and titled "Orthopaedic Implants," the entire contents of which are incorporated herein by reference.

TECHNICAL FIELD

This disclosure relates to identification of landmarks on orthopaedic implants.

BACKGROUND

Orthopaedic implants, such as the interlocking nail, have significantly widened the scope for intramedullary (IM) fixation of bone fractures. Anchoring an IM nail to a bone makes the construct more stable longitudinally and stops rotation of the nail within the bone. A typical IM nail fixation surgery involves a combination of jigs, x-ray imaging, and manual "eye-balling" to locate and drill the distal screw holes and to install the screws in the screw holes.

In IM nail fixation surgery, an IM nail is inserted into the canal of a fractured long bone in order to fixate the fractured ends together. Typically, the proximal locking is performed first and is usually carried out with a jig. Nail deformation during intramedullary insertion and manufacturing capabilities, however, may make a jig inaccurate for the distal screws. In fact, the positioning of the distal locking screws and alignment of the drill for the drilling of the distal screw holes is the most time consuming and challenging step of the implantation procedure. The two main reasons for failure in distal locking are (1) incorrect entry point on the bone and (2) wrong orientation/trajectory of the drill. If either of these problems occurs, then the drill will not go through the nail hole.

An inaccurate entry point also compounds the problem as the rounded end of the drill bit often slips, damaging healthy bone rendering it difficult to place another drill hole next to the inaccurate hole. Inaccurate distal locking may lead to premature failure with breakage of the nail through the nail hole, breakage of the screw, or the breaking of the drill bit within the bone.

In order to overcome the problems associated with distal locking, instrumented IM nails have been designed for distal locking. The instrumented IM nails include a probe having one or more sensors connected to one or more processors. Calibration of the IM nail is carried out to insure that the spatial relationship between the one or more magnetic sensors and one or more landmarks, such as screw holes on the IM nail, are known and accurate. Once calibrated, the IM nail is packaged for use, and the sensor(s) must maintain their position and orientation relative to the landmarks in order for the IM nail to be properly secured within the body of a patient. Limiting or preventing movement of the probe and the associated sensor(s) relative to the IM nail and/or the landmark(s) following calibration and packaging, and prior to use, has been a challenge.

Using adhesives to glue the probe and associated sensor(s) to the IM nail, and in particular, to a groove formed in the IM nail, have been an accepted technique for preventing movement of the probe and sensor(s) relative to the IM nail and landmark(s). Use of adhesives, however, have made it very difficult, and in most cases, impossible, to remove the probe, associated sensor(s), and adhesive following surgery. This has led to increased inventory and parts costs and has prohibited reuse of costly materials.

There remains a need for a solution that provides features or structures to the IM nail, and in particular, a groove formed in the IM nail, that sufficiently capture the probe and associated sensor(s) following calibration of the IM nail. Further, a need exists for insuring that the position and orientation of the sensor(s) relative to the landmark(s) on the IM nail remain set for targeting and locking of the IM nail within the body, and for providing for easy removal of the probe and associated sensor(s) after targeting and/or locking of the IM nail so that the probe and sensor(s) may be cleaned and reused again. Moreover, a need exists for an implant that includes a probe and associated sensor captured in a manner that permits targeting and locking of a driving end of the implant prior to fixation of the non-driving end.

SUMMARY

In a general aspect, an orthopaedic implant includes a body defining at least one landmark and a probe including a sensor spaced apart from the at least one landmark a set distance. The probe and sensor being releasably fixed to the body of the implant to limit movement of the sensor relative to the at least one landmark.

Implementations may include one or more of the following features. For example, the implant includes a longitudinal groove defined along an outer surface of the body, the longitudinal groove including a driving end portion and a non-driving end portion. The sensor is located in the non-driving end portion of the longitudinal groove. The longitudinal groove includes at least two side walls and a floor connecting the two side walls. The longitudinal groove includes at least a portion along a length of the longitudinal groove wherein the two side walls each form an acute angle with the floor. The longitudinal groove includes at least a second portion along the length of the longitudinal groove wherein the two side walls each form an angle of 90 degrees or greater with the floor. A length of the portion wherein the two side walls each form an acute angle with the floor is between about 0.025 inches to about 0.5 inches. The longitudinal groove receives the probe and sensor in one of a releasable interference fit, press fit, friction fit, or snap fit. The longitudinal groove receives the probe and sensor in a clearance fit and the probe is coupled to the driving end of the groove. The probe is prevented from rotation and translation within the groove. The implant further includes a cover over at least a portion of the groove. The cover is laser-welded to at least a portion of one of the groove and the implant.

At least a portion of the longitudinal groove includes one of a dovetail, polygonal, oval, keyhole, or circular cross-sectional shape. The longitudinal groove is configured to receive the probe such that an outer surface of the probe is positioned at or below an outer surface of the body of the implant. The groove includes an opening to the outer surface of the implant and the opening has a width which is less than a diameter of the probe. The landmark is selected from the group consisting of a structure, a hole filler, a polymer screw hole window such as PEEK, a void, a boss, a channel, a detent, a flange, a groove, a member, a partition a step, an aperture, a bore, a cavity, a dimple, a duct, a gap, a notch, an orifice, a passage, a slit, a hole, or a slot.

The implant further includes an element having a body with an outwardly extending formation, and wherein the longitudinal groove further includes a recess or through-hole defined in the groove configured to receive the outwardly extending formation. The outwardly extending formation is received in the recess or through-hole via a snap-fit connection or screw-in connection. The probe includes one of an elongated polymer tape or a printed circuit board in contact with the body of the element such that the probe can be separated from at least a portion of the element following implantation of the implant. A portion of the body of the element that is attached to the probe is perforated to permit separation of the probe from the element.

The implant further includes a film shrink-wrapped around the probe and the body of the implant to releasably secure the probe and sensor to the implant. The film includes a set of perforations to permit separation of the probe and the sensor from the implant following implantation of the implant into a body. The probe includes an outwardly extending formation that is configured to pierce the shrink-wrapped film when brought into contact with the film. The film is made from a biodegradable or biocompatible material. The tear strength of the film is lowest along the line parallel to the long axis of the probe In another general aspect, a method includes releasably fixing a probe including a sensor to an orthopaedic implant such that the sensor is spaced apart from at least one landmark defined in the orthopaedic implant a set distance, and calibrating the sensor such that a spatial relationship is known between the sensor and the at least one landmark.

Implementations may include one or more of the following features. For example, fixing the probe includes placing the probe in a clearance fit in a longitudinal groove on the surface of the implant and coupling a driving end of the probe to the implant such that the probe is prohibited from rotating and translating within the groove. The method further includes placing a cover over at least a portion or preferably the entire length of the groove. Placing the cover includes laser-welding the cover to one of the implant and the groove. The method further includes removing the probe and the sensor from the orthopaedic implant following implantation of the implant into a body. Releasably fixing the probe and the sensor to the implant includes placing at least a portion of the probe into at least one longitudinal section of a longitudinal groove formed in the implant, the at least one longitudinal section of the longitudinal groove configured to receive the probe in one of a interference fit, press fit, friction fit, or snap fit. The probe includes one of an elongated polymer tape or a printed circuit board, and releasably fixing the probe and sensor to the implant includes securing an element having a body with an outwardly extending formation into a recess defined in a longitudinal groove formed in the implant via a snap-fit connection, and coupling the probe and sensor to the body of the element such that the probe and sensor can be separated from at least a portion of the element. Releasably fixing the probe and sensor to the implant includes shrink-wrapping a film around the probe and the body of the implant to releasably secure the probe and sensor to the implant.

In another general aspect, an intramedullary nail includes a body defining at least one screw hole, a longitudinal groove with a driving end portion and a non-driving end portion formed along an outer surface of the body, and a probe including a sensor. The probe is releasably secured within the longitudinal groove such that the sensor is spaced apart from the at least one screw hole a set distance.

Implementations may include one or more of the following features. For example, the longitudinal groove includes at least two side walls and a floor connecting the two side walls. The longitudinal groove includes a first portion along a length of the longitudinal groove wherein the two side walls each form an acute angle with the floor and a second portion along the length of the longitudinal groove wherein the two side walls each form an angle of approximately 90 degrees or greater with the floor. The longitudinal groove retains the probe at or below the outer surface of the implant. The groove includes an opening to the outer surface of the implant and the opening has a width which is less than a diameter of the probe. The groove further includes a cover. The cover is laser-welded to at least one of the implant and the groove. The probe is prevented from rotating and translating within the groove.

The nail further includes an element having a body with an outwardly extending formation, and wherein the longitudinal groove further includes a recess defined in the longitudinal groove and configured to receive the outwardly extending formation via a snap-fit connection. The probe includes one of an elongated polymer tape or a printed circuit board being in contact with the body of the element such that the probe can be separated from at least a portion of the element following implantation of the intramedullary nail. A portion of the body of the element that is attached to the probe is perforated to permit separation of the probe from the element.

The nail further includes a film shrink-wrapped around the probe and the body of the nail to releasably secure the probe and sensor to the nail. The film includes a set of perforations to permit separation of the probe and the sensor from the nail following implantation of the nail into a body. The probe includes an outwardly extending formation that is configured to pierce the shrink-wrapped film when brought into contact with the film. The film is made from a biodegradable or biocompatible material. The tear strength of the film is lowest along a line parallel to a long axis of the probe The disclosed apparatuses and methods include several advancements. For example, the disclosed apparatuses and methods provide features and structures that sufficiently capture a probe and associated sensor(s) in a calibrated position and orientation to permit the instrumented IM nail to perform its designed targeting function, yet allow for easy removal of the probe and sensor(s) after targeting. This permits reuse of the probe and sensor(s) with other IM nails, lowers inventory costs, and reduces the number of parts and materials required to be left behind in the body of a patient. Moreover, the disclosed apparatuses and methods provide features that permit locking of the nail at the driving end of the implant prior to locking or fixing the non-driving end of the implant. In addition, the disclosed apparatuses and methods assist in limiting or preventing tissue from dislodging or causing the probe and associated sensor to translate or rotate in the groove during, for example, insertion of the IM nail into the body of the patient. Further, the disclosed apparatuses and methods provide features and structures that limit or eliminate bone-in growth in the groove and thus, allow the implant to be removed easily later during revision surgery or when a new implant is required.

Other advantages and features will be apparent from the following detailed description when read in conjunction with the attached drawings.

It should be understood that the drawings are not necessarily to scale and that the disclosed implementations are sometimes illustrated diagrammatically and in partial views. In certain instances, details which are not necessary for an understanding of the disclosure or which render other details difficult to perceive may have been omitted. It should be understood, of course, that this disclosure is not limited to the particular implementations illustrated herein.

DETAILED DESCRIPTION

Figure 1:
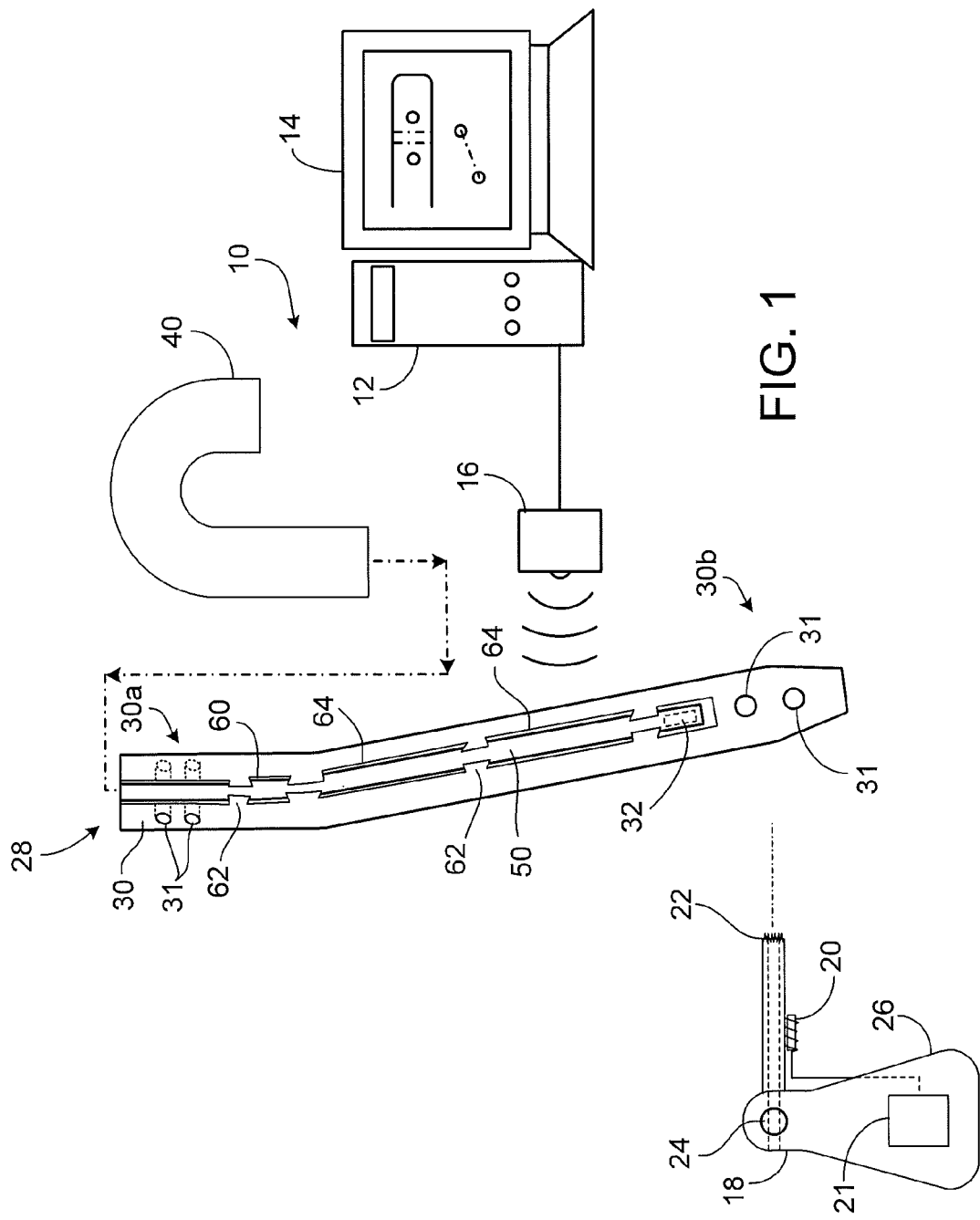
FIG. 1 illustrates a system for identifying a landmark.

Referring to the accompanying drawings in which like reference numbers indicate like elements, FIG. 1 illustrates one disclosed system 10 for identifying a landmark. The system 10 includes a processor 12, a magnetic field generator 16, a landmark identifier 18, and an orthopaedic implant assembly 28. The system 10 also includes a monitor 14 electrically connected to the processor 12 and an insertion handle 40 removably attached to an orthopaedic implant 30 of the orthopaedic implant assembly 28, and in a particular example, to a driving end 30a opposite a non-driving end 30b of the orthopaedic implant 30. The processor 12 is depicted as a desktop computer in FIG. 1 but other types of computing devices may be used. As examples, the processor 12 may be a desktop computer, a laptop computer, a personal data assistant (PDA), a mobile handheld device, or a dedicated device. The magnetic field generator 16 is a device available from Ascension Technology Corporation of 107 Catamount Drive, Milton Vt., U.S.A.; Northern Digital Inc. of 103 Randall Drive, Waterloo, Ontario, Canada; or Polhemus of 40 Hercules Drive, Colchester Vt., U.S.A. Of course, other generators may be used. As examples, the field generator 16 may provide a pulsed direct current electromagnetic field or an alternating current electromagnetic field. The system 10 may also include a control unit (not shown) connected to the magnetic field generator 16. The control unit controls the field generator 16, receives signals from small mobile inductive sensors, and communicates with the processor 12, either by wire or wirelessly. The control unit may be incorporated into the processor 12 either through hardware or software.

The system 10 may be referred to as a magnetic position tracking system. For illustrative purposes, the system 10 may include a magnetic field generator 16 comprised of suitably arranged electromagnetic inductive coils that serve as the spatial magnetic reference frame (i.e., X, Y, Z). The system 10 may also include small mobile inductive sensors, which are attached to the object being tracked. It should be understood that other variants could be easily accommodated. The position and angular orientation of the small mobile inductive sensors are determined from its magnetic coupling to the source field produced by magnetic field generator 16.

It is noted that the magnetic field generator 16 generates a sequence, or set, of six, different spatial magnetic field shapes, or distributions, each of which is sensed by the small mobile inductive sensors. Each sequence enables a sequence of signals to be produced by the small mobile inductive sensors. Processing of the sequence of signals enables determination of position and/or orientation of the small mobile inductive sensors, and hence the position of the object to which the small mobile inductive sensor is mounted relative the magnetic coordinate reference frame which is in fixed relationship to the magnetic field generator 16. The processor 12 or the control unit may use the reference coordinate system and the sensed data to create a transformation matrix comprising position and orientation information.

The landmark identifier 18 is used to target a landmark, such as a landmark on the orthopaedic implant assembly 28. The landmark identifier 18 may include one or more small mobile inductive sensors or may include the field generator. The landmark identifier 18 has a second sensor 20. The landmark identifier 18 may be any number of devices. As examples, the landmark identifier may be a device that includes a structure that provides a user with an understanding of the location and orientation of a hidden landmark. For example, the landmark identifier can include a drill guide, a drill sleeve, a drill, a drill nose, a drill barrel, a drill chuck, or a fixation element. In some implementations, the structure can be a housing having an opening, or other structure that indicates the location and orientation of a landmark. In FIG. 1, the landmark identifier 18 is a drill sleeve and includes a sensor 20. The landmark identifier 18 may include one or more of a serrated tip 22, a tube 24, and a handle 26. The tube 24 also may be referred to as a bushing, cylinder, guide, or drilling/screw placement guide. The second sensor 20 is oriented relative to an axis of the tube 24. The tube 24 may receive a drill. This offset of the sensor 20 from the tube 24 allows the position and orientation of the tube to be located in space in six dimensions (three translational and three angular) relative to the magnetic field generator 16 and/or another sensor in the system. The processor 12 may need to be calibrated to adjust for the offset distance of the second sensor 20. The landmark identifier 18 and the field generator 16 may be combined into a single component. For example, the field generator 16 may be incorporated within the handle 26.

Figure 1A:
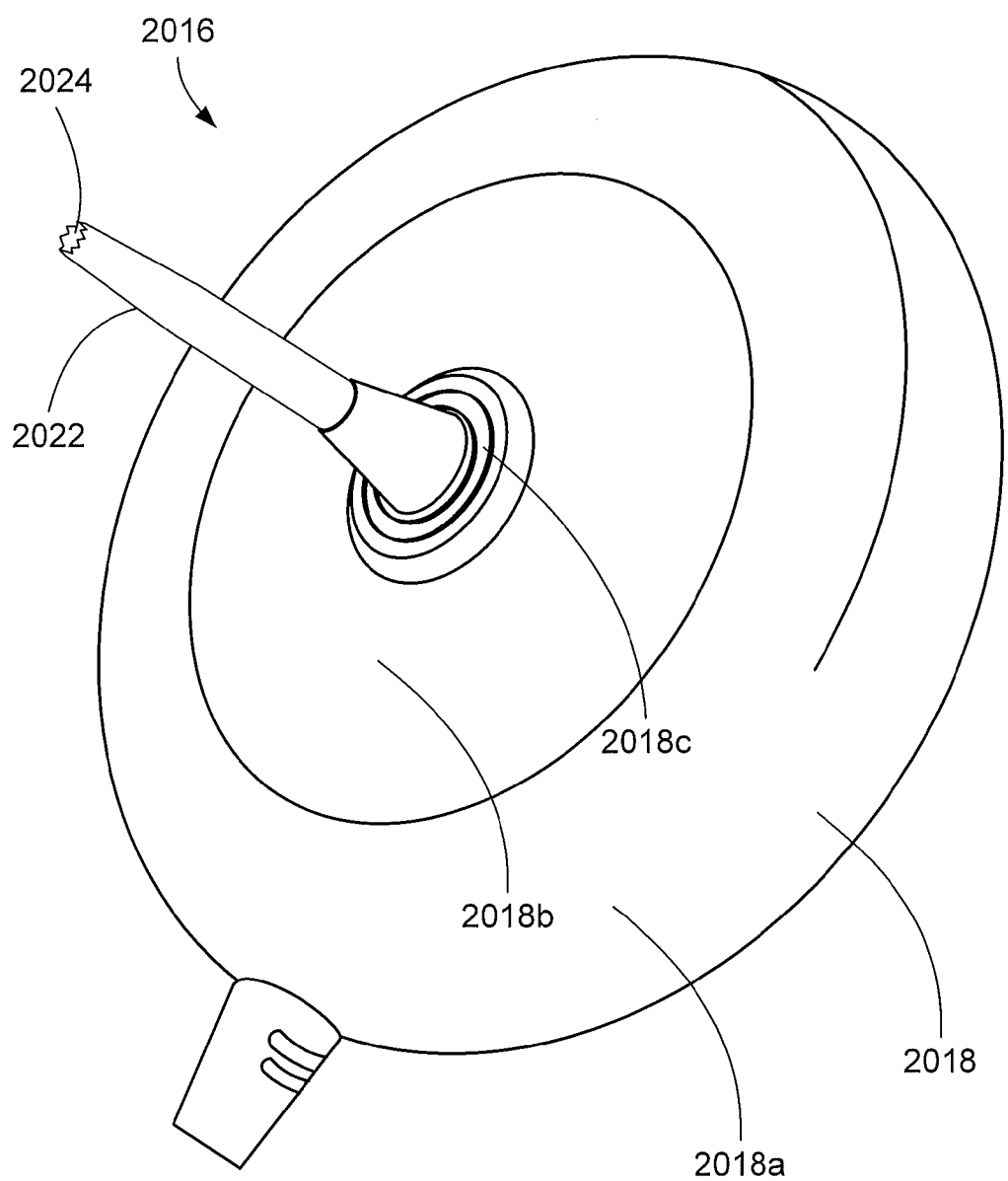
FIG. 1A illustrates an alternative implementation of a landmark identifier for use in the system of FIG. 1.

FIG. 1A illustrates an alternative implementation that combines the functionalities of the landmark identifier 18 and the field generator 16 with a removable component, such as a drill sleeve 2022, into a handheld landmark identifier 2016 that may be used in the system 10. The handheld landmark identifier 2016 houses an electromagnetic field generator (not shown) that may include one or more induction coils or other elements to create a suitable electromagnetic field or fields. The electromagnetic field generator is mounted in or on an autoclavable material and encapsulated in an autoclavable housing body 2018 that may be easily sterilized. The housing body 2018 includes a coupling member 2018c that passes through the internal body and the housing 2018 and removably engages one or more attachable components, such as drill sleeve 2022 having a serrated tip 2024, or other suitable tools, such as a screw driver sleeve or other drill sleeves as selected by a surgeon. The housing body 2018 includes a first covering 2018a formed from an autoclavable material, such as an overmolding of silicone material, and may include a second covering 2018b that provides an additional layer of protection or insulation, or aesthetics at an outer edge of the housing 2018. The second covering 2018b may be formed from an autoclavable material similar or different than the first covering 2018a.

Unlike the landmark identifier 18 illustrated in FIG. 1, the handheld landmark identifier 2016 does not require the sensor 20 because the origin of the global space (the area in which the electromagnetic field is generated) can be defined within the landmark identifier 2016. For example, one axis of the global space coordinate system can be the longitudinal axis of the drill sleeve or other component 2022. In that situation, the other two axes of the global space coordinate system can be defined by planes orthogonal to that longitudinal axis and to each other. An advantage of incorporating the field generator into the landmark identifier 2016 includes a smaller size field generator because it can be brought into the local working space (area which may include the landmarks such as implant holes that are to be targeted for screw placement), therefore requiring a smaller electromagnetic field. In addition, use of the landmark identifier 2016 eliminates the necessity of X-ray devices for targeting of transfixion elements, such as radiation-emitting, fluoroscopic "c-arms," which have been used during tibial and femoral nail cases to achieve proper distal screw placement.

The orthopaedic implant assembly 28 may include the implant 30 and one or more small mobile inductive sensors. In the implementation shown in FIGS. 1 and 2, the orthopaedic implant assembly 28 includes a probe 50 disposed within a longitudinal groove 60 formed in the implant 30. The probe 50 includes a tape body 51 and a first sensor 32 disposed within or on the tape body 51. The probe 50 is disposed within the groove 60. The tape body 51 of the probe 50 may have a rectangular, circular, oval, or square geometry to assist in orienting the tape body 51 as it is placed into the implant 30, and the geometry may be constant or varying along a length of the probe 50. In some implementations, the tape body 51 may be a hollow metal tube. The probe 50 may include a lead or wire (not shown) coupled to the first sensor 32 to transmit, for example, a signal from the first sensor 32 to the processor 12. The lead may be made from biocompatible wire. As an example, the lead may be made of DFT wire available from Fort Wayne Metals Research Products Corp., 9609 Indianapolis Road, Fort Wayne, Ind. 46809. DFT is a registered trademark of Fort Wayne Metals Research Products Corp. Alternatively, the first sensor 32 may be coupled to the processor 12 via a wireless connection.

Figure 2:
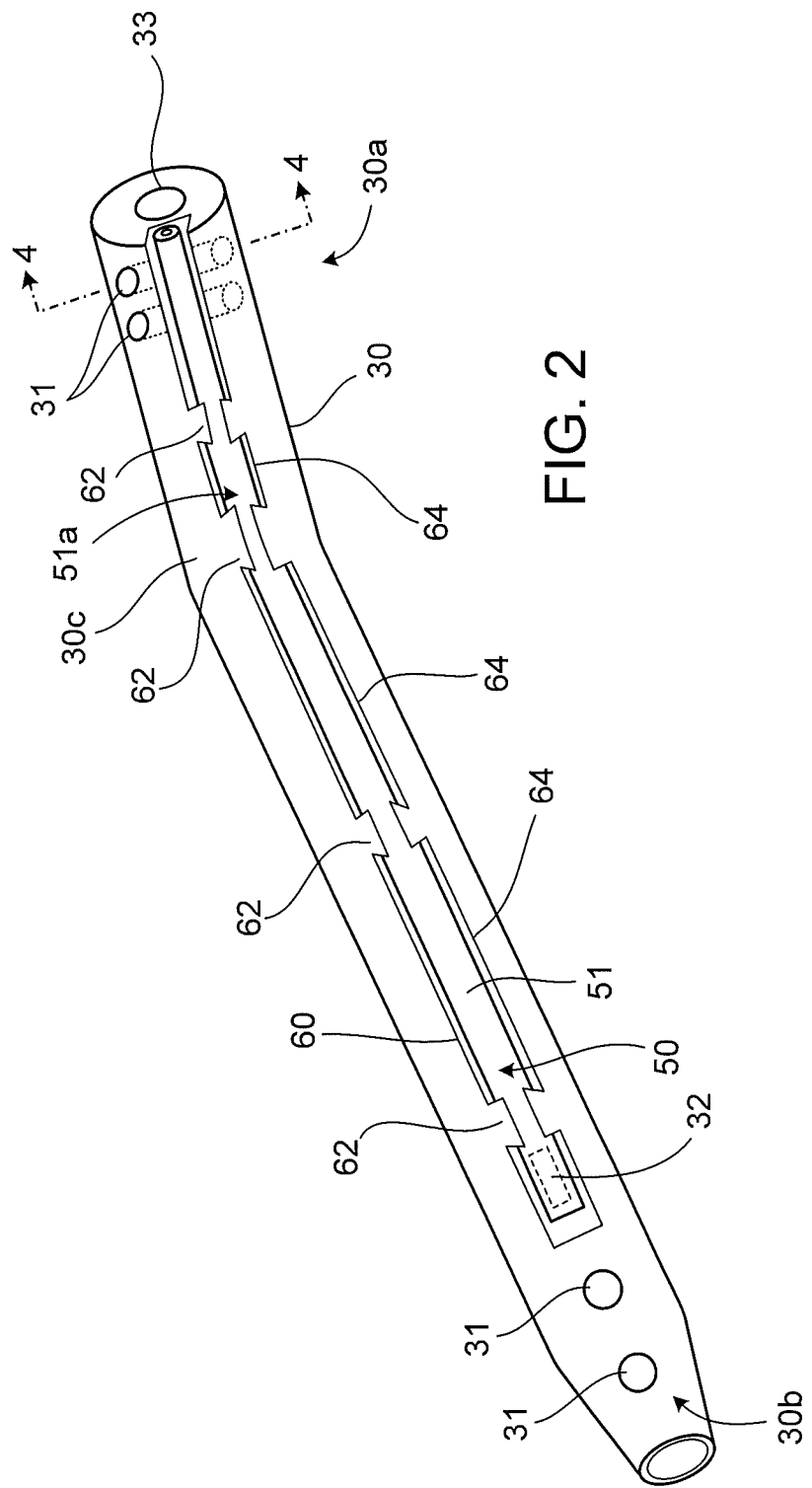
FIG. 2 is a detailed prospective view of the orthopaedic implant of FIG. 1.

In FIGS. 1 and 2, the implant 30 is in the form of IM nail but other types of implants may be used. As examples, the implant may be an IM nail, a bone plate, a shoulder prosthetic, a hip prosthetic, or a knee prosthetic. The implant 30 may be made from any suitable biocompatible material, such as, titanium, cobalt chrome, stainless steel, biodegradable polymer, or other biocompatible material. The implant 30 may include a cannulation 33.

The first sensor 32 is oriented and in a predetermined position relative to one or more landmarks on the implant 30. As examples, the landmark may be a structure, a void, a boss, a channel, a detent, a flange, a groove, a member, a partition, a step, an aperture, a bore, a cavity, a dimple, a duct, a gap, a notch, an orifice, a passage, a slit, a hole, or a slot. In addition, the landmark may be a hole filler, a polymer screw hole window such as PEEK, or other identifier formed in or on the implant 30 that identifies or indicates the location on the implant 30 through which a surgeon may form a through hole or other aperture during implantation for receiving a fixation member, such as a screw. In FIGS. 1 and 2, the landmarks are transfixion holes 31. The offset of the first sensor 32 from the landmark allows the position of the landmark to be located in space in six dimensions (three translational and three angular) relative to the magnetic field generator 16 or another sensor in the system, such as the second sensor 20. The processor may need to be calibrated to adjust for the offset distance of the first sensor 32.

The first sensor 32 and the second sensor 20 are coupled to the processor 12. Again, this may be accomplished by wire or wirelessly. The first sensor 32 and the second sensor 20 may be a six degree of freedom sensor configured to describe the location of each sensor in three translational axes, generally called X, Y and Z and three angular orientations, generally called pitch, yaw and roll. By locating the sensor in these reference frames, and knowing the location and orientation of each sensor, the landmark identifier 18 may be located relative to the landmark on the implant 30. In one particular implementation, the information from the sensors allows for a surgeon to plan the surgical path for fixation and properly align a drill with a blind fixation hole 31. Exemplary sensors 32, 20 are six degrees of freedom sensor from Ascension Technology Corporation of 107 Catamount Drive, Milton Vt., U.S.A.; Northern Digital Inc. of 103 Randall Drive, Waterloo, Ontario, Canada; or Polhemus of 40 Hercules Drive, Colchester Vt., U.S.A. Of course, other sensors may be used.

As shown in FIGS. 1 and 2, the probe 50, which includes the tape body 51 and the first sensor 32 disposed within or on the tape body 51, are disposed within the longitudinal groove 60 formed in an outer surface of the implant 30. The groove 60 extends from a driving end 30a of the implant 30 to a non-driving end 30b of the implant 30 so that the first sensor 32 may be placed in a desired proximity to the landmarks 31 to be targeted. Of course, the groove 60 may be located anywhere along the length of the implant 30 in order to position the first sensor 32 within the desired proximity to the landmarks 31. Further, although the first sensor 32 is shown positioned near the landmarks 31 formed in the non-driving end 30b of the implant 30, the first sensor 32 may be positioned near the landmarks 31 formed in the driving end 30a of the implant 30. In this manner, having the probe 50 within groove 60, instead of within the central cannula 33, permits locking of the implant 30 using the landmarks 31 at the driving end 30a of the implant 30 prior to affixing the implant 30 at the non-driving end 30b.

Figure 3:
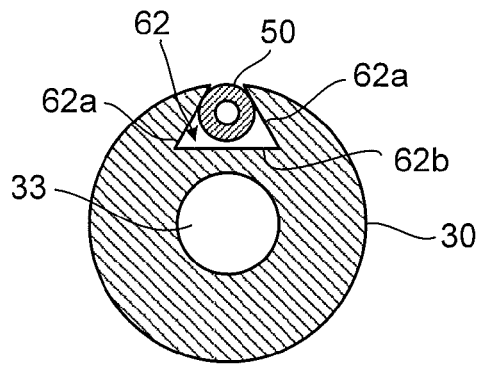
FIG. 3 is a cross-sectional view of the orthopaedic implant taken along one of the portions 62 of the orthopaedic implant of FIG. 2.
Figure 5:
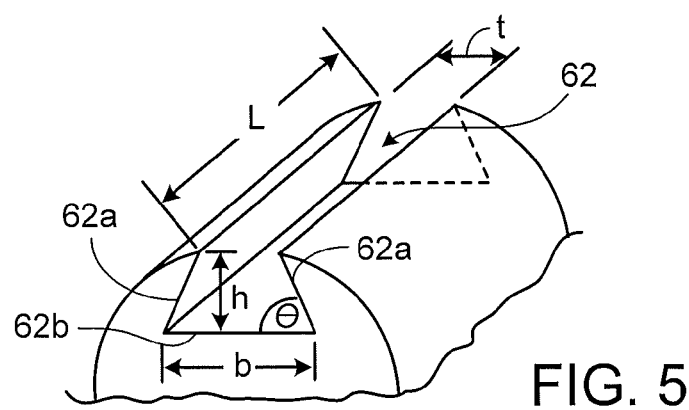
FIG. 5 is an enlarged view of one of the portions 62 of the orthopaedic implant of FIG. 2.

The groove 60 may include one or more portions 62 formed at intermittent locations along the length of the groove 60 to receive the probe 50, and more particularly, the tape body 51, in order to rigidly and mechanically capture the probe 50 and the first sensor 32 in a fixed position relative to the implant 30. For example, as shown in FIGS. 3 and 5, the portions 62 include two side walls 62a and a floor 62b intersecting the two side walls 62a. The walls 62a form an acute angle θ with the floor 62b such that a cross section of the portion 62 forms a dovetail when viewed from an end of the groove 60 (FIG. 3). These dovetail-shaped side walls 62a and floors 62b provide an interference, press, friction, or snap fit between the probe 50 and the groove 60 by pressing the sections of the probe 50 received in the portions 62 against the floor 62b.

The force to capture the probe 50 in a position and orientation relative to the implant 30, and the force required to remove the probe 50 from the groove 60, for example, upon completion of targeting the landmarks 31, depends on a number of factors. These factors include the length (l) of each dovetail portion 62, the opening width (t), height (h), and floor width (b) of each dovetail side wall portion 62 (FIG. 5), and the location and number of dovetail portions 62 along the length of the groove 60. As an example, the optimization of the length (l) of each dovetail portion 62 provides a balance between the force required to snap or press the probe 50 into each of the portions 62 and the force to remove the probe 50 following targeting. In an exemplary implementation, the length (l) is about 0.025 inch to about 0.5 inch, or alternatively, about 0.075 inch to about 0.15 inch, the height (h) of each portion 62 is about 0.055 inch, the opening width (t) is about 0.078 inch, and the floor width (b) is about 0.083 inch. The ratios of the height (h), the opening width (t), and the floor width (b) to, for example, the diameter of the probe 50, in some implementations, are in the range of about 65% to about 73%, about 92% to about 96%, and at least 100% respectively.

The groove 60 may have as many as five to six dovetail portions 62 along its length, and in some implementations, a portion 62 is positioned to correspond to the location on the probe 50 where there is a change in a radial angle along the probe axis to insure that the probe 50 remains secured within the groove 60 within the transition portion of the implant 30. For example, as shown in FIG. 2, implant 30 includes at least one transition section 30c that forms an angle between the driving end 30a and the non-driving end 30b of the implant 30. At least one dovetail portion 62 is positioned within transition section 30c to ensure that the probe 50 is secured within the transition section 30c. In other implementations, a minimum of one to two dovetail portions 62 may be sufficient to fix the probe 50 and the first sensor 32 in place relative to the implant 30. In implementations where only one dovetail portion 62 is provided in the groove 60, the dovetail portion 62 may be positioned near the driving end 30a of the implant 30 to secure the probe 50 within the groove 60.

Figure 4:
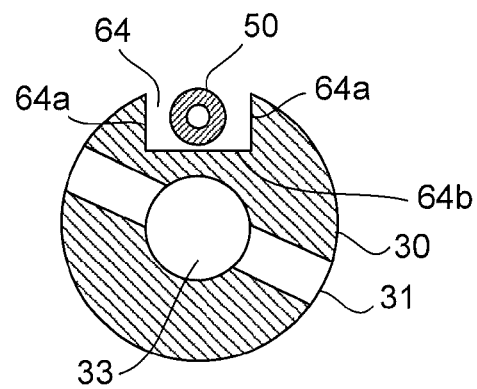
FIG. 4 is a cross-section view of the orthopedic implant taken along portion 4-4 of FIG. 2.

Referring to FIGS. 2 and 4, in addition to the one or more dovetail portions 62, the groove 60 may include one or more portions 64 formed adjacent to the dovetail portions 62 and at intermittent locations along a length of the groove 60. Like the portions 62, the portions 64 may include two side walls 64a and a floor 64b intersecting the two side walls 64a. The side walls 64a may form right angles with the floor 64b such that a cross section of the portion 62 is substantially square or rectangular when viewed from an end of the groove 60 (FIG. 4). Other implementations where the side walls form angles greater than 90 degrees with the floor are also within the scope of the invention. As shown in FIG. 4, unlike portions 62, the probe 50 does not interact with the side walls 64a of the portions 64. However, in other implementations, the dimensions of the side walls 64a and the floor 64b may be sized such that the side walls 64a and the floor 64b interact with the probe 50 to provide, for example, an additional interference fit between the side walls 64a and/or the floor 64b.

Figure 3A:
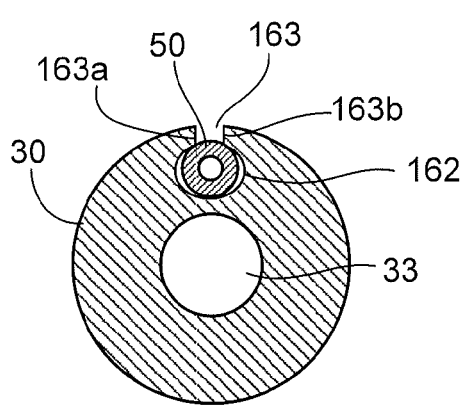
FIG. 3A is a cross-sectional view of the orthopaedic implant taken along one of the portions 62 of the orthopaedic implant of FIG. 2.

An alternative implementation of groove 60, and specifically, portions 62, is shown in FIG. 3A. In the implementation of FIG. 3A, portions 162 are formed with a substantially circular cross-sectional shape (when viewed from an end of the groove 60) that receives the probe 50. The portions 162 include an opening 163 formed between two walls 163a, 163b for receiving the probe 50 within the circular cross-sectional area of the portions 162. The opening 163 has a width which is less than a diameter of the probe 50. End portions of the walls 163a, 163b provide an interference, press, friction, or snap fit between the probe 50 and the groove 60 to maintain the probe 50 in position within the portions 162 and to limit movement of the probe 50 caused, for example, by tissue grabbing or dislodging the probe during, for example, insertion of the implant 30 in a bone.

Figure 4A:
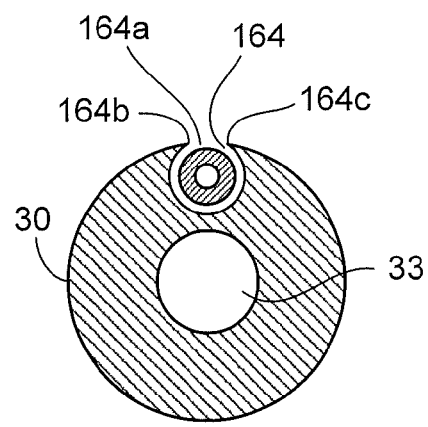
FIG. 4A is a cross-section view of the orthopedic implant taken along one of the portions 64 of the orthopaedic implant of FIG. 2.

Referring to FIGS. 3A and 4A, in addition to the one or more circular portions 162, the groove 60 may include one or more circular portions 164 formed adjacent to the portions 162 and at intermittent locations along a length of the groove 60. Like the portions 162, the portions 164 are formed with a substantially circular cross-sectional shape (when viewed from an end of the groove 60) that receives the probe 50. As shown in FIG. 4A, unlike portions 162, the probe 50 is free to move within the portions 164. However, in other implementations, the dimensions of the circular portion 164 may be sized such that the probe 50 interacts with portions of the opening 164a formed by end portions 164b, 164c of the implant 30 to provide, for example, an additional interference fit between the probe 50 and the portions 164. As illustrated in FIGS. 3A and 4A, when received within the portions 162, 164, the outer surface of the probe 50 is positioned at or below the outer surface of the body of the implant 30, which assists in preventing or limiting tissue from dislodging or causing the probe 50 to translate or rotate during, for example, insertion of the implant 30 in a bone. In certain implementations, however, it may also be positioned above the outer surface of the implant 30, if necessary.

In use, the probe 50, including the first sensor 32, is secured within the groove 60 of the implant 30, by pressing or snapping the probe 50 into the one or more dovetail portions 62 formed in the longitudinal groove 60. The implant 30 may then be calibrated. Calibration is analogous to registration in computer assisted surgery. Calibration may be needed for different reasons. For example, sensor calibration may be needed to correct for manufacturing tolerances. The system may be designed based upon a computer-aided-design model, and calibration is used to accurately place the sensors relative to one another or to the one or more landmarks 31. For example, calibration may be necessary to determine the spatial relationship between the first sensor 32 and one or more of the landmarks 31. The processor or the control unit may include software to generate X, Y, Z, pitch, yaw, and roll offset values to locate the sensors in a global coordinate system or simply placement relative to one another. The system may be manufactured and calibrated during manufacturing and assigned a unique identifier, such as a serial number, color code, bar code, or RFID tag. If the system needs to be re-calibrated, the unique identifier may be used to retrieve the offset values, either locally or over a network. Further, the unique identifier may be used to retrieve other data, such as the size of the IM nail or the length of the IM nail and/or the probe.

Following calibration, the implant 30 may be packaged and shipped to an end user, such as a physician, who then performs an implantation procedure. During shipping and implantation of the implant 30, the probe 50 and the first sensor 32 are secured within the groove 60 via an interference or snap fit between the dovetail portions 62 and the probe 50, as described above. Once targeting of one or more of the landmarks 31 is complete, the probe 50 and the first sensor 32 may be removed from the implant 30 and sterilized for reuse with another implant 30.

Figure 6:
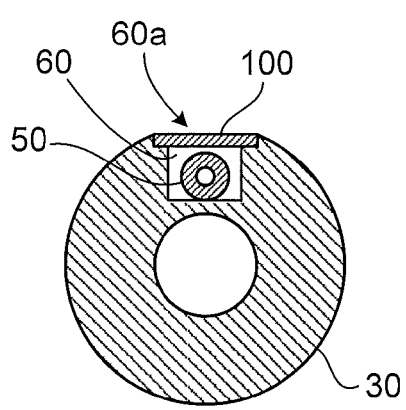
FIG. 6 is a cross-sectional view of an alternative implementation of the orthopaedic implant assembly 28.

FIG. 6 illustrates an alternative implementation of the orthopaedic implant assembly 28 including the orthopaedic implant 30. As shown in FIG. 6, the probe 50 and associated sensor, such as sensor 32, are received in the longitudinal groove 60 formed in the implant 30. Similar to the other implementations discussed above, the groove 60 may extend from the driving end 30a of the implant 30 to the non-driving end 30b of the implant. The groove 60 may include an additional cut-out portion 60a located near the outer portion of the implant 30 as shown in FIG. 6. A lid or cover 100 may be attached to the implant 30 within the groove 60, and particularly within the cut-out portion 60a of the groove 60. The lid or cover 100 may be attached within the cut-out portion 60a of the groove 60 by laser-weld, gluing, or other acceptable attachment means. In another implementation, the lid or cover 100 may be attached to the implant 30, for example, to an outer surface of the implant 30. The lid or cover 100 prevents bone in-growth in the groove 60 and thus, allows the implant to be removed easily later during, for example, revision surgeries or when a new implant is required. The lid or cover 100 also prevent tissue from touching the probe 50 during installation of the implant 30 into the body and therefore, may also assist in preventing rotation or translation of the probe 50.

Figure 7:
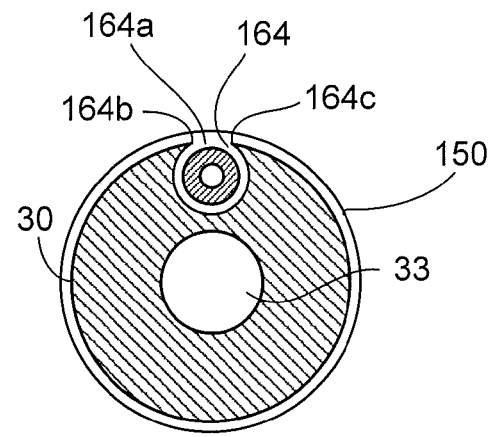
FIG. 7 is a cross-sectional view of an alternative implementation of the orthopaedic implant assembly 28.
Figure 7A:
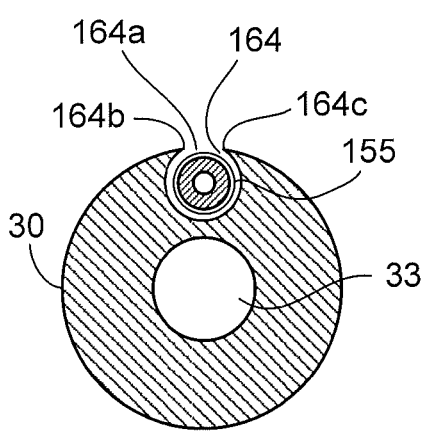
FIG. 7A is a cross-sectional view of an alternative implementation of the orthpaedic implant assembly 28.

FIG. 7 shows an alternative to the cover or lid 100 of FIG. 6 for preventing bone in-growth in the groove. As shown in FIG. 7, an outer sleeve 150 may be placed around the periphery or a portion of the periphery of the orthopaedic implant 30. The outer sleeve 150 may be coupled to the implant 30 via press fit or other means known to one skilled in the art. The outer sleeve 150 covers over the groove 60, and acts as the lid 100 of FIG. 6 to prevent bone in-growth in the groove 60, following, for example removal of the probe 50 from the groove 60 following implantation of the implant 30 into bone tissue. The outer sleeve 150 can include one or more longitudinal slits so long as it can grab on the implant 30 and cover the groove 60. Although the outer sleeve 150 is shown as encircling the periphery of the implant 30, the outer sleeve 150 may encircle only a portion of the periphery of the implant 30 as long as the outer sleeve 150 can attach to the implant 30 or groove 60 and cover the groove opening. Alternatively, a similar sleeve 155 (FIG. 7A) can be used in place of the outer sleeve 150 and adapted to be placed around the periphery or a portion of the periphery of the probe 50. The sleeve 155 can include one or more longitudinal slits, and can cover only a portion of the periphery of the probe 50 so long as the sleeve 155 can cover the groove opening. In the implementation of FIG. 7A, the probe 50 and the sleeve 155 are, for example, press-fitted in the groove 60. The sleeve 155 acts in a similar manner to the lid 100 of FIG. 6 to prevent bone in-growth in the groove 6 following, for example, removal of the probe 50 from the groove 60.

Figure 8:
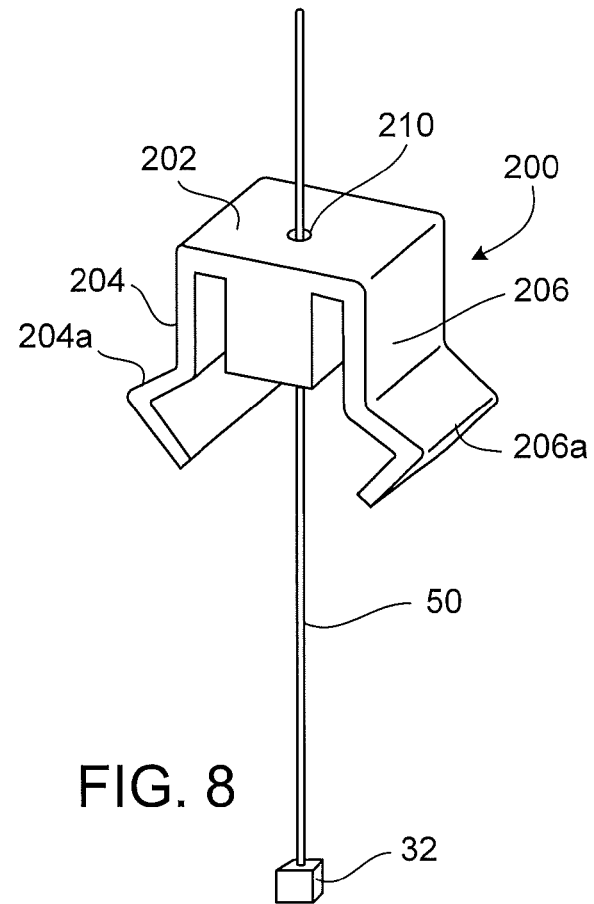
FIG. 8 is an alternative implementation for limiting or preventing translation and rotation of the probe 50 within the groove 60.

FIG. 8 illustrates a coupling mechanism for coupling the probe 50 to the implant 30 for limiting or preventing translation and rotation of the probe 50 and associated sensor 32 within the groove 60 relative to the implant 30. As shown in FIG. 8, a retention mechanism 200 includes a body portion 202 with an anti-rotation cross section such as a rectangular cross section as shown and two leg portions 204, 206 extending from the body portion 202. In one implementation, the leg portions 204, 206 include generally V-shaped, deflectable portions 204a, 206a configured and shaped to mate with mating portions (such as corresponding grooves, voids or receptacles (not shown)) formed within the groove 60. As shown in FIG. 8, the retention mechanism 200 defines a through hole 210 through which the probe and included sensor may pass and be retained via glue, crimping, friction fitting or any attachment means known to one skilled in the art.

In use, the retention mechanism 200 may be inserted, for example, into the longitudinal groove 60 at the driving end 30a of the implant 30 by compressing the leg portions 204, 206 towards each other. As the retention mechanism 200 is inserted into the longitudinal groove 60, the leg portions 204, 206 ride along the inside surface of the longitudinal groove 60 until the V-shaped portions 204a, 206a are positioned proximate the corresponding mating portions (not shown) formed within the groove 60. Once the leg portions 204, 206 are proximate the mating portions, the leg portions 204, 206 rebound towards their uncompressed state and interact with their respective corresponding mating portions such that the retention mechanism 200, and the attached probe and sensor are prevented or limited from translating or rotating relative to the implant 30. Once targeting of one or more of the landmarks 31 is complete, the retention mechanism 200, and the attached probe 50 and sensor, may be removed from the implant 30 by compressing the leg portions 204, 206 such that they no longer interact with the corresponding mating portions formed in the groove 60, and the retention mechanism 200, probe 50 and sensor may be removed from the implant 30 and sterilized for reuse with another implant 30.

Figure 9:
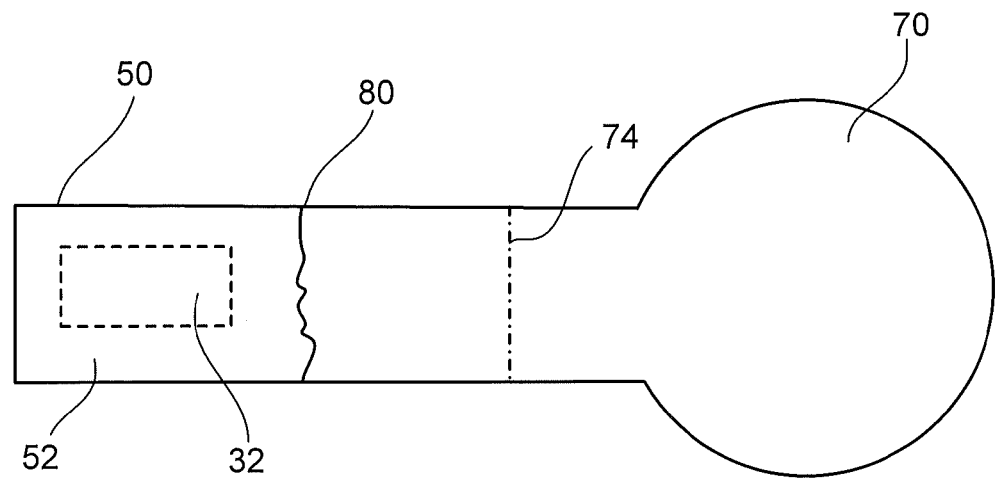
FIG. 9 is a top view of a bushing for use in an alternative implementation of the orthopaedic implant.
Figure 10:
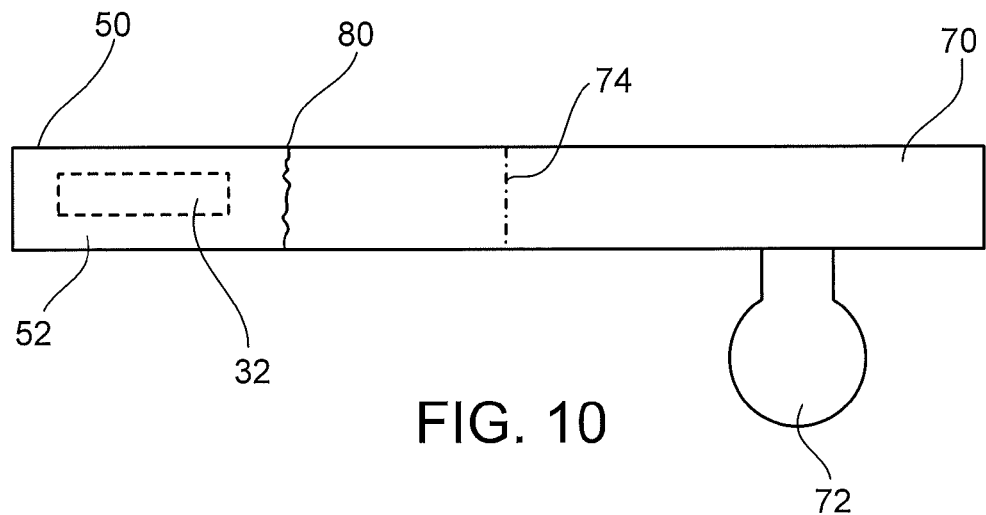
FIG. 10 is a side view of the bushing of FIG. 6.
Figure 11:
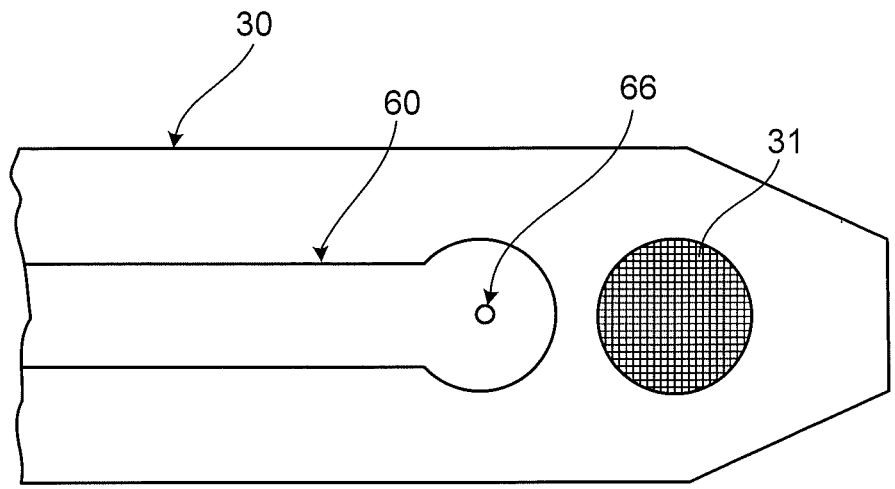
FIG. 11 is a top view of the alternative implementation of the orthopaedic implant.
Figure 12:
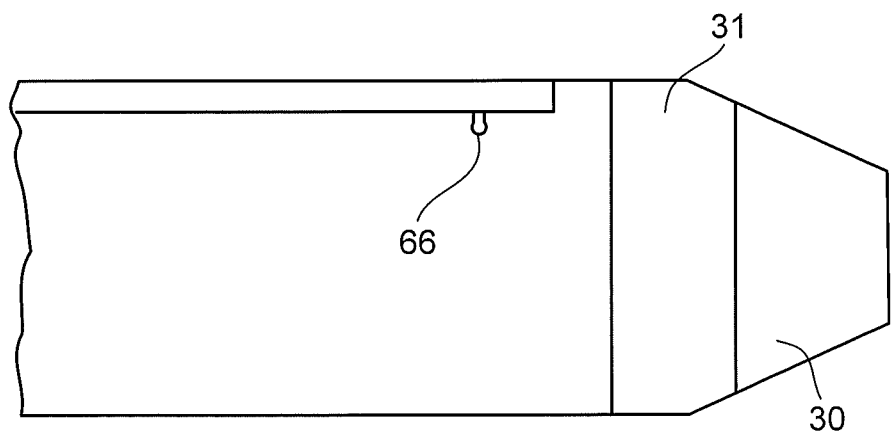
FIG. 12 is a cross-sectional view of the orthopaedic implant of FIG. 8 taken along a longitudinal axis of the implant.

FIGS. 9-12 illustrate an alternative implementation of the orthopaedic implant assembly 28 including an orthopaedic implant 30. As shown in FIGS. 11 and 12, the implant 30 includes at least one landmark in the form of a transfixion hole 31. The implant 30 includes a longitudinal groove 60 formed in a portion of the implant 30. The groove 60 may be formed along an outer surface of the implant 30. FIGS. 9 and 10 illustrate an element in the form of a bushing 70 that can be made from a biocompatible and/or biodegradable material, such as a biocompatible and biodegradable polyethylene or other suitable material. The bushing 70 includes an outwardly extending spherical nipple 72 that is received in a corresponding recess 66 defined in the groove 60 in a snap-fit arrangement.

The assembly 28 includes a probe 50 in the form of an elongated polymer tape or printed circuit board 52 and a first sensor 32 disposed within or on the tape or printed circuit board 52. The tape or board 52 may also include wires (not shown) coupled to the first sensor 32 to transmit, for example, a signal from the first sensor 32 to the processor 12. The tape or board 52 is coupled to, and in contact with, the bushing 70 via a bond 80. Bond 80 may be formed by welding, gluing, or otherwise coupling and contacting the tape or board 52, including the first sensor 32, to the bushing 70. The bushing 70 further includes a perforation 74 that permits separation of the tape or board 52 and the first sensor 32 from the bushing 70 following, for example, targeting of the landmark 31. The perforation may be adapted to require a smaller force of breakage than that of the probe/tape.

In use, following calibration, and during shipping and implantation of the implant 30, the tape or board 52 and the first sensor 32 are secured within the groove 60 via the bushing 70. Once targeting of the one or more of the landmarks 31 is complete, the tape or board 52 and the first sensor 32 may be separated and removed from the implant 30 by separating the tape or board 52 from a portion of the bushing 70 via the perforations 74. The tape or board 52 and the first sensor 32 may then be sterilized for reuse with another implant 30 and bushing 70, or simply discarded.

Figure 13:
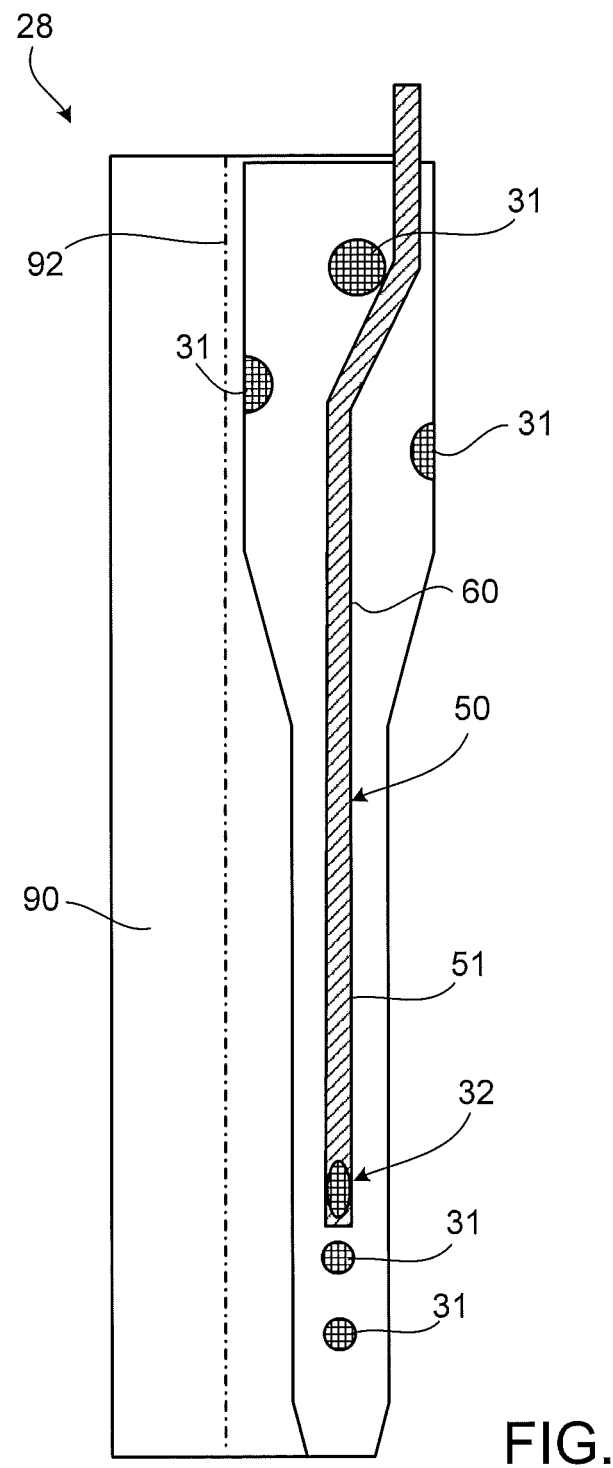
FIG. 13 illustrates another implementation of a orthopaedic implant assembly.

FIG. 13 illustrates another implementation of the orthpaedic implant assembly 28 including the orthopaedic implant 30. The implant 30 includes landmarks in the form of transfixion holes 31. The implant 30 includes a longitudinal groove 60 formed on an outer surface of the implant 30, however, the longitudinal groove is optional. The assembly 28 includes a probe 50, which includes a tape body 51 and a first sensor 32 disposed within or on the tape body 51. A portion of the tape body 51 and the sensor 32 may be positioned within the groove 60. The groove 60 extends from a driving end 30a of the implant 30 to a non-driving end 30b of the implant 30 so that the first sensor 32 may be placed in a desired proximity to any of the landmarks 31 to be targeted.

The implant assembly 28 further includes a biodegradable and/or biocompatible polymer film 90. The film 90 may be made from any suitable biocompatible and/or biodegradable polymer material, such as, but not limited to, polylactic acid (PLA) or polyglycolide or polyglycolic acid (PGA). Once the probe 50 (tape body 51 and the first sensor 32) are placed on the surface of the implant 30, such as within the groove 60, the implant 30 and the probe 50 are shrink-wrapped with the film 90 to limit and/or prevent movement of the probe 50 and sensor 32 relative to the implant 30.

In order to remove the probe 50 from the implant 30 following, for example, targeting of the one or more landmarks 31, the film 90 may be manufactured to include a one-way tear (not shown) or a set of perforations 92 to allow for separation of the probe 50 from the implant 30 through the shrink-wrapped film 90. Alternatively, the probe 50 may be provided with an outwardly extending formation (not shown), such as a sharp edge or protrusion that pierces and/or cuts the shrink-wrapped film 90 as the probe 50 is pulled and separated from the implant 30. As a further alternative, the film 90 may be made from a molecularly-oriented polymer having a minimal tear strength along one direction or axis within the film. In such an implementation, the film 90 may be oriented on the implant 30 such that when the film is wrapped around the implant 30, the minimal tear axis is lined up with, or parallel to, the longitudinal axis of the probe 50, such that, upon removal of the probe 50 from the implant 30, the film 90 tears along the longitudinal axis of the probe 50 allowing for ease of removal from the implant 30.

While only certain implementations have been set forth, alternatives and modifications will be apparent from the above description to those skilled in the art. For example, although the portions 62 of the groove 60 have been described as having a dovetail-like cross-sectional shape, other shapes are within the scope of this disclosure. For example, alternative cross-sectional shapes include polygonal, oval, keyhole, or circular. In addition, the cross-sectional shape of portions 62 may be similar to the cross-sectional shape of portions 64 yet smaller in size such that the probe 50 is received in the portions 62 in an interference fit. In addition, the portions 62 may include protrusions added to, or formed as an integral part of the groove 60, that provide a balanced force between rigidly and mechanically capturing the probe 50 and allowing for the release of the probe 50 upon completion of use. These and other alternatives are considered equivalents and within the spirit and scope of this disclosure and the appended claims.

The invention claimed is:

1. An orthopaedic implant comprising:
a body defining at least one landmark, the body defining a longitudinal groove along an outer surface of the body, the longitudinal groove comprising a driving end portion and a non-driving end portion and having a length along the driving end portion and non-driving end portion, wherein the longitudinal groove is defined at least in part by side walls and a floor connecting the side walls;
a probe comprising a sensor, the sensor being spaced apart from the at least one landmark a set distance, the probe and sensor being releasably fixable to the body of the implant to limit movement of the sensor relative to the at least one landmark; and
wherein the body comprises multiple discrete receiving portions configured to releasably fix the probe to the body, the receiving portions being spaced apart along the length of the longitudinal groove, wherein each of the discrete receiving portions comprises a portion of one of the side walls that is shaped to press a section of the probe received in the receiving portion against the floor.

2. The implant of claim 1, wherein the body defines a cannula that extends generally parallel to the longitudinal groove, the longitudinal groove being offset from the cannula; and
wherein the body comprises a wall that separates the cannula from the longitudinal groove.

3. The implant of claim 1, wherein the sensor is located in the non-driving end portion of the longitudinal groove.

4. The implant of claim 1, wherein longitudinal groove comprises at least a portion along the length of the longitudinal groove wherein the side walls each form an acute angle with the floor.

5. The implant of claim 4, wherein the longitudinal groove comprises at least a second portion along the length of the longitudinal groove wherein the side walls each form an angle of approximately 90 degrees or greater with the floor.

6. The implant of claim 4, wherein a length of the portion where the side walls each form an acute angle with the floor is between about 0.025 inches to about 0.5 inches.

7. The implant of claim 1, wherein the longitudinal groove receives the probe and sensor in one of a releasable interference fit, press fit, friction fit, or snap fit.

8. The implant of claim 1, wherein the longitudinal groove receives the probe and sensor in a clearance fit and the probe is coupled to the driving end of the groove.

9. The implant of claim 8, wherein the probe is prevented from rotation and translation within the groove.

10. The implant of claim 8, further comprising a cover for the groove.

11. The implant of claim 10, wherein the cover is laser-welded to at least a portion of one of the groove and the implant.

12. The implant of claim 1, wherein at least a portion of the longitudinal groove comprises one of a dovetail, polygonal, oval, keyhole, or circular cross-sectional shape.

13. The implant of claim 1, wherein the longitudinal groove is configured to receive the probe such that an outer surface of the probe is positioned at or below an outer surface of the body of the implant, wherein each of the discrete receiving portions comprises a structure that extends into or over a portion of the longitudinal groove to releasably fix a portion of the probe in the longitudinal groove.

14. The implant of claim 13, wherein the groove comprises an opening to the outer surface of the implant, wherein the opening is located along the length of the groove along at a particular receiving portion of the receiving portions, and wherein the opening has a width perpendicular to the length of the groove, and the width of the opening at the particular receiving portion is less than a diameter of the probe that is received in the particular receiving portion.

15. The implant of claim 14, wherein the opening to the outer surface of the implant extends along the length of the longitudinal groove proximally beyond the particular retaining portion and distally beyond the particular retaining portion, and
wherein, at locations that are proximal and distal to the particular retaining portion and are adjacent to the particular retaining portion, the opening has a width perpendicular to the length of the longitudinal groove that is equal to or greater than the diameter of the probe.

16. The implant of claim 1, wherein the landmark is selected from the group consisting of a structure, a hole filler, a polymer screw hole window, a void, a boss, a channel, a detent, a flange, a groove, a member, a partition a step, an aperture, a bore, a cavity, a dimple, a duct, a gap, a notch, an orifice, a passage, a slit, a hole, or a slot.

17. The implant of claim 1, wherein the longitudinal groove comprises an opening to the outer surface of the implant, the opening extending to the outer surface of the implant along the driving end portion of the longitudinal groove, along the non-driving end portion of the longitudinal groove, and from the driving end portion of the longitudinal groove to the non-driving end portion of the longitudinal groove.

18. The implant of claim 1, the body has proximal portion, a distal portion, and a transition section forming an obtuse angle between the proximal portion and the distal portion,
wherein at least one of the retaining portions is located at or adjacent to the transition section.

19. The implant of claim 1, wherein the body defines a recess at the non-driving end portion of the longitudinal groove; and
wherein the probe has a bushing located distal to the sensor, the bushing having an extension configured to mate with the recess to secure the bushing to the body,
the bushing having a perforation located between the extension and the sensor, wherein the bushing has a force of breakage at the perforation that is less than a force of breakage of portions of the probe located proximal to the perforation.

20. A method comprising:
releasably fixing a probe comprising a sensor to an orthopaedic implant such that (i) the sensor is spaced apart from at least one landmark defined in the orthopaedic implant a set distance, and (ii) discrete receiving portions spaced apart along a length of the orthopaedic implant releasably retain the probe in the orthopaedic implant; and
after releasably fixing the probe to the orthopaedic implant, calibrating the sensor to determine a spatial relationship between the sensor and the at least one landmark.

21. The method of claim 20, wherein fixing the probe includes placing the probe in a clearance fit in a longitudinal groove formed in the implant and coupling a driving end of the probe to the implant such that the probe is limited from rotating and translating within the groove.

22. The method of claim 21, further comprising removing the probe and the sensor from the orthopaedic implant following implantation of the implant into a body.

23. The method of claim 20, wherein releasably fixing the probe and the sensor to the implant comprises placing at least a portion of the probe into at least one longitudinal section of a longitudinal groove formed in the implant, the at least one longitudinal section of the longitudinal groove configured to receive the probe in one of a interference fit, press fit, friction fit, or snap fit.

24. The method of claim 20, wherein the orthopaedic implant an outer surface and a longitudinal groove defined along the length of the orthopaedic implant, the longitudinal groove having an opening that extends through the outer surface along at least a portion of the length of the orthopaedic implant, and
wherein releasably fixing a probe comprising a sensor to the orthopaedic implant comprises pressing or snapping the probe into the longitudinal groove through the opening in a direction transverse to the length of the orthopaedic implant.

25. The method of claim 20, wherein the orthopaedic implant has a driving end and a non-driving end, and an exterior side extending from the driving end to the non-driving end, wherein the orthopaedic implant has a longitudinal groove extending along the exterior side, and
wherein releasably fixing a probe comprising a sensor to the orthopaedic implant comprises moving the probe from outside the orthopaedic implant into the longitudinal groove through the exterior side.

26. The method of claim 20, further comprising:
after calibrating the sensor, implanting the orthopaedic implant into a patient's body;
while the orthopaedic implant is implanted in the patient's body, using the determined spatial relationship and data from the sensor to locate the at least one landmark; and
after locating the at least one landmark, removing the probe from the orthopaedic implant while the orthopaedic implant remains implanted in the patient's body.

27. The method of claim 20, wherein calibrating the sensor comprises:
determining offset values that indicate the spatial relationship between the sensor and the at least one landmark; and
storing the offset values in association with an identifier corresponding to the orthopaedic implant to which the sensor is releasably fixed.

28. An intramedullary nail comprising:
a body defining at least one screw hole;
a longitudinal groove with a driving end portion and a non-driving end portion formed along an outer surface of the body, wherein the longitudinal groove is defined at least in part by side walls and a floor connecting the side walls; and
a probe comprising a sensor, the probe being releasably securable in the longitudinal groove such that the sensor is spaced apart from the at least one screw hole a set distance,
wherein the body comprises discrete receiving portions that are configured to releasably secure the probe in the longitudinal groove, the receiving portions being located at intermittent locations along the longitudinal groove,
wherein each of the discrete receiving portions comprises a structure that extends into or over a portion of the longitudinal groove to releasably secure a portion of the probe in the longitudinal groove, wherein each of the discrete receiving portions comprises a portion of one of the side walls that is shaped to press a section of the probe received in the receiving portion against the floor.

29. The intramedullary nail of claim 28, wherein one or more of the receiving portions comprises at least two substantially planar side walls and a substantially planar floor that extends from one of the substantially planar side walls to the other of the substantially planar side walls and connects the at least two substantially planar side walls, the longitudinal groove comprising a first portion along a length of the longitudinal groove wherein the at least two substantially planar side walls each form an acute angle with the substantially planar floor and a second portion along the length of the longitudinal groove wherein the at least two substantially planar side walls each form an angle of approximately 90 degrees or greater with the substantially planar floor.

30. The intramedullary nail of claim 28, wherein the longitudinal groove comprises an opening that extends to the outer surface of the intramedullary nail along at least a portion of the longitudinal groove, and
wherein the receiving portions are configured to retain the probe in the longitudinal groove at or below the outer surface of the intramedullary nail such that the probe does not extend through the opening.

31. The intramedullary nail of claim 28, wherein the longitudinal groove has a length that extends along the non-driving end portion and the driving end portion, the longitudinal groove having an opening defined through the outer surface of the body along the length of the longitudinal groove,
wherein the receiving portions are intermittently located along the length of the longitudinal groove and the receiving portions are separated by other portions of the body that are located adjacent the receiving portions,
wherein the opening has a width perpendicular to the length, and the width of the opening at the receiving portions is smaller than the width of the opening at the other portions.

32. The intramedullary nail of claim 28, wherein the longitudinal groove has an opening through the outer surface of the body, the opening extending along a length of the longitudinal groove,
wherein the receiving portions define portions of the opening at the outer surface and are dimensioned to limit passage of the probe through the outer surface at the opening, and
wherein the body comprises other portions located adjacent to the receiving portions along the length of the longitudinal groove, and the other portions defining portions of the opening at the outer surface that admit the probe through the outer surface without limiting passage of the probe through opening.

33. The intramedullary nail of claim 28, wherein each of the discrete receiving portions comprises structures that extend into or over the longitudinal groove from opposing sides of the longitudinal groove and define an opening between the structures, wherein the longitudinal groove has a continuous opening along a length of the longitudinal groove, wherein the continuous opening extends across each of the discrete receiving portions.

34. The intramedullary nail of claim 28, wherein the intramedullary nail has an opening at an end of the intramedullary nail,
wherein the longitudinal groove extends along an axis and the longitudinal groove extends to the opening at the end of the intramedullary nail, and
wherein the opening at the end of the intramedullary nail permits the probe to be removed from the intramedullary nail through the opening in a direction along the axis.

\* \* \* \* \*